US011752257B2

(12) United States Patent
Hwang et al.

(10) Patent No.: US 11,752,257 B2
(45) Date of Patent: Sep. 12, 2023

(54) ACTIVATION SYSTEM AND METHOD FOR ON-BODY MEDICAL DEVICES

(71) Applicant: Becton, Dickinson and Company, Franklin Lakes, NJ (US)

(72) Inventors: Charles George Hwang, Wellesley, MA (US); J. Richard Gyory, Sudbury, MA (US); Joseph Gordon, Mansfield, MA (US); Kenneth Focht, Needham, MA (US); Stanislav Torgovitsky, Washington, DC (US); Stacey J. Longanecker, Glenn Dale, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 25 days.

(21) Appl. No.: 17/542,218

(22) Filed: Dec. 3, 2021

(65) Prior Publication Data
US 2022/0105262 A1  Apr. 7, 2022

Related U.S. Application Data

(62) Division of application No. 15/506,923, filed as application No. PCT/US2015/049099 on Sep. 9, 2015, now Pat. No. 11,229,737.
(Continued)

(51) Int. Cl.
*A61M 5/142* (2006.01)
*G16H 40/63* (2018.01)
(Continued)

(52) U.S. Cl.
CPC .... *A61M 5/14248* (2013.01); *A61M 5/16831* (2013.01); *G16H 40/63* (2018.01);
(Continued)

(58) Field of Classification Search
CPC .............. A61M 5/142; A61M 5/14248; A61M 5/16831; A61M 5/1424; A61M 5/14244;
(Continued)

(56) References Cited

U.S. PATENT DOCUMENTS 3,668,337 A  6/1972 Sinclair
4,349,712 A  9/1982 Michalski
(Continued)

FOREIGN PATENT DOCUMENTS

CN  103394143 A  11/2013
CN  103415310 A  11/2013
(Continued)

OTHER PUBLICATIONS

Canadian Office Action dated Apr. 16, 2021, which issued in the corresponding Canadian Patent Application No. 2,960,223.
(Continued)

*Primary Examiner* — Emily L Schmidt
*Assistant Examiner* — Alexandra Lalonde
(74) *Attorney, Agent, or Firm* — Dickinson Wright PLLC

(57) ABSTRACT

A medical device for infusing medical substances has activation buttons accessible on an exterior of a device housing. The activation buttons and corresponding electrical switches within the housing are configured to prevent inadvertent activation of the buttons and therefore inadvertent operation of the switches to initiate a process such as medical substance delivery to a user. The device employs overlap of respective time traces initiated by activation of the activation buttons to determine whether the activation is intended and valid. The respective time traces do not have to be initiated simultaneously or in any particular sequence. The activation buttons can be elastomeric overmolded buttons set within cutouts in the housing, and, when depressed, make physical contact with respective switches.

8 Claims, 20 Drawing Sheets

Related U.S. Application Data

(60) Provisional application No. 62/048,733, filed on Sep. 10, 2014.

(51) Int. Cl.
   G16Z 99/00 (2019.01)
   A61M 5/168 (2006.01)

(52) U.S. Cl.
   CPC ... *G16Z 99/00* (2019.02); *A61M 2005/16863* (2013.01); *A61M 2205/276* (2013.01); *A61M 2205/3386* (2013.01); *A61M 2205/3584* (2013.01); *A61M 2205/50* (2013.01); *A61M 2205/502* (2013.01); *A61M 2205/582* (2013.01); *A61M 2205/8206* (2013.01)

(58) Field of Classification Search
   CPC .............. A61M 5/168; A61M 2205/52; A61M 2205/27; A61M 2205/276; A61M 2205/3386; A61M 2205/3584; A61M 2205/50; A61M 2205/502; A61M 2205/582; A61M 2205/8206; A61M 2005/16863; A61M 2005/14272; A61M 2005/14292; A61M 2005/14288; G16H 20/17; G16H 20/10; G16H 20/00; G16H 20/13
   See application file for complete search history.

(56) References Cited

U.S. PATENT DOCUMENTS

| | | |
|---|---|---|
| 4,766,271 A | 8/1988 | Mitsuhashi et al. |
| 5,136,131 A | 8/1992 | Komaki |
| 5,399,823 A | 3/1995 | McCusker |
| 5,665,065 A | 9/1997 | Colman et al. |
| 6,093,900 A | 7/2000 | Wisskirchen et al. |
| 6,603,086 B2 | 8/2003 | Kawaguchi et al. |
| 6,747,446 B1 | 6/2004 | Voisine et al. |
| 6,841,748 B2 | 1/2005 | Serizawa et al. |
| 7,094,985 B2 | 8/2006 | Kobayashi et al. |
| 7,435,922 B1 | 10/2008 | Wittig et al. |
| 7,708,717 B2 | 5/2010 | Estes et al. |
| 7,771,391 B2 | 8/2010 | Carter |
| 7,884,295 B2 | 2/2011 | Aoki et al. |
| 7,922,708 B2 | 4/2011 | Estes et al. |
| 8,062,253 B2 | 4/2011 | Nielsen et al. |
| 8,008,591 B2 | 8/2011 | Shi et al. |
| 8,094,806 B2 | 1/2012 | Levy |
| 8,114,064 B2 | 2/2012 | Alferness et al. |
| 8,184,023 B2 | 5/2012 | Naka et al. |
| 8,226,606 B2 | 7/2012 | Adams et al. |
| 8,226,607 B2 | 7/2012 | Carter et al. |
| 8,231,572 B2 | 7/2012 | Carter et al. |
| 8,242,922 B2 | 8/2012 | Varasteh |
| 8,263,889 B2 | 9/2012 | Takahashi et al. |
| 8,267,921 B2 | 9/2012 | Yodfat et al. |
| 8,414,563 B2 | 4/2013 | Kamen et al. |
| 8,455,778 B2 | 6/2013 | Yang et al. |
| 8,469,920 B2 | 6/2013 | Mernoe et al. |
| 8,540,673 B2 | 9/2013 | Hines et al. |
| 8,653,392 B2 | 2/2014 | Berger et al. |
| 8,810,438 B2 | 8/2014 | Tsai et al. |
| 8,894,632 B2 | 11/2014 | Yodfat et al. |
| 9,192,713 B2 | 11/2015 | Yodfat et al. |
| 2002/0092753 A1 | 7/2002 | Asada |
| 2003/0160683 A1 | 8/2003 | Blomquist |
| 2009/0065342 A1 | 3/2009 | Yoon et al. |
| 2009/0237275 A1 | 9/2009 | Vaganov |
| 2009/0247982 A1 | 10/2009 | Krulevitch et al. |
| 2009/0281497 A1 | 11/2009 | Kamen et al. |
| 2011/0022025 A1 | 1/2011 | Savoie |
| 2011/0319862 A1 | 12/2011 | Friedman et al. |
| 2011/0320184 A1 | 12/2011 | Beyer |
| 2012/0061226 A1 | 3/2012 | Edo et al. |
| 2012/0215175 A1 | 8/2012 | Alferness et al. |
| 2012/0253262 A1* | 10/2012 | Lemke ............... A61N 1/30 604/20 |
| 2013/0072872 A1* | 3/2013 | Yodfat ............... A61M 5/168 604/131 |
| 2013/0114195 A1 | 5/2013 | Lee |
| 2013/0332874 A1 | 12/2013 | Rosinko |
| 2014/0088504 A1 | 3/2014 | King |
| 2014/0262715 A1 | 9/2014 | Lee et al. |
| 2016/0000366 A1 | 1/2016 | Jensen |
| 2017/0239415 A1 | 8/2017 | Hwang et al. |

FOREIGN PATENT DOCUMENTS

| | | |
|---|---|---|
| CN | 103477314 A | 12/2013 |
| EP | 3191155 A1 | 7/2017 |
| GB | 2234115 A | 1/1991 |
| JP | 64-40793 | 2/1989 |
| JP | 01183022 A | 7/1989 |
| JP | 06231652 A | 8/1994 |
| JP | 6678654 B2 | 4/2020 |
| WO | 2012108723 A2 | 8/2012 |
| WO | 2016040423 A1 | 3/2016 |

OTHER PUBLICATIONS

Chinese of Office Action dated Mar. 18, 2020, which issued in the corresponding Chinese Patent Application No. 201580052982.1, including English translation.

English translation of the Japanese Office Action dated Jul. 2, 2019, which issued in the corresponding Japanese Patent Application No. 2017-513452.

Chinese Office Action dated Feb. 19, 2019, which issued in corresponding Chinese Patent Application No. 201580052982.1, English translation.

Supplementary Partial European Search Report daled Apr. 24, 2018, which issued in the counterpart Patent Application No. 15840926.8.

* cited by examiner

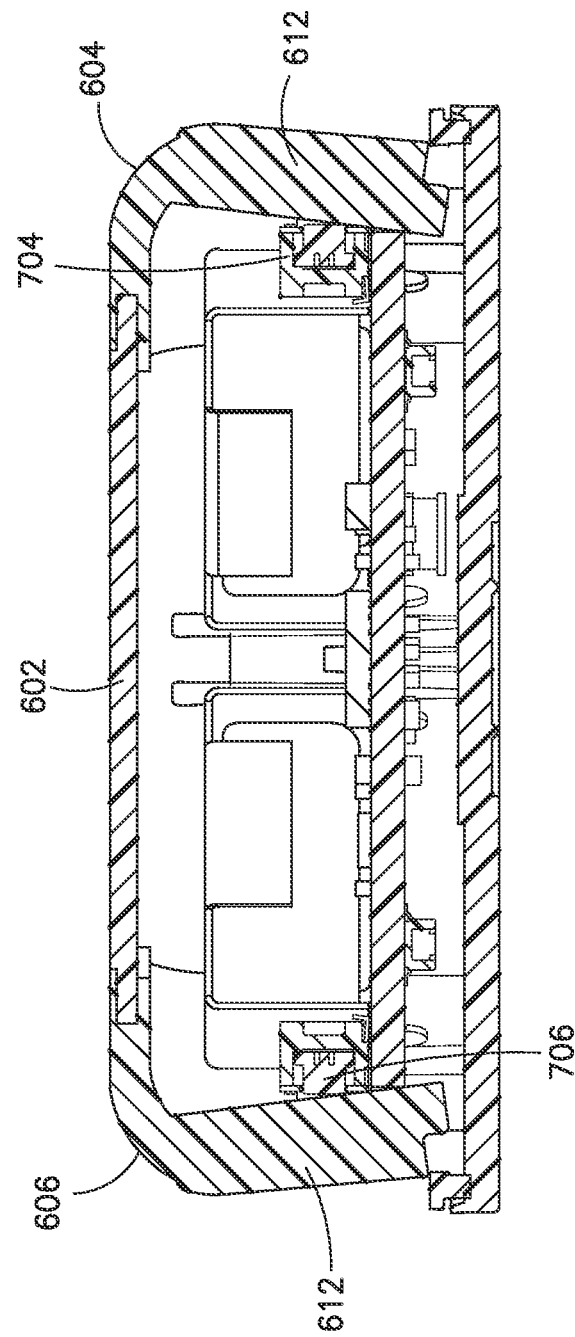

ACTIVATION SYSTEM AND METHOD FOR ON-BODY MEDICAL DEVICES

This application is a divisional of U.S. patent application Ser. No. 15/506,923, filed Feb. 27, 2017, which is based on PCT Application No. PCT/US2015/049099 filed Sep. 9, 2015, which claims the benefit of U.S. Provisional Application Ser. No. 62/048,733, filed Sep. 10, 2014, the entire contents of which are incorporated herein by reference.

FIELD OF THE INVENTION

The present invention relates generally to medical devices, and more particularly, to wearable or on-body medicine delivery devices that require the device user to initiate the delivery of medicine.

BACKGROUND OF THE INVENTION

Diabetes is a group of diseases characterized by high levels of blood glucose resulting from the inability of diabetic patients to maintain proper levels of insulin production when required. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient. Type 1 diabetes (T1D) patients are required to take insulin (e.g., via injections or infusion) to move glucose from the bloodstream because their bodies generally cannot produce insulin. Type 2 diabetes (T2D) patients generally can produce insulin but their bodies cannot use the insulin properly in order to maintain blood glucose levels within medically acceptable ranges. In contrast to people with T1D, the majority of those with T2D usually do not require daily doses of insulin to survive. Many people are able to manage their condition through a healthy diet and increased physical activity or oral medication. However, if they are unable to regulate their blood glucose levels, they will be prescribed insulin. For example, there are an estimated 6.2 million Type 2 diabetes patients (e.g., in the United States, Western Europe and Canada) taking multiple-daily-injections (MDI) which consist of a 24-hour basal insulin and a short acting rapid insulin that is taken at mealtimes for glycemic management control.

For the treatment of Type 1 diabetes (T1D) and sometimes Type 2 diabetes (T2D), there are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

Another effective method for insulin therapy and managing diabetes is infusion therapy or infusion pump therapy in which an insulin pump is used. The insulin pump can provide continuous infusion of insulin to a diabetic patient at varying rates in order to more closely match the functions and behavior of a properly operating pancreas of a non-diabetic person that produces the required insulin, and the insulin pump can help the diabetic patient maintain his/her blood glucose level within target ranges based on the diabetic patient's individual needs. Infusion pump therapy requires an infusion cannula, typically in the form of an infusion needle or a flexible catheter, that pierces the diabetic patient's skin and through which infusion of insulin takes place. Infusion pump therapy offers the advantages of continuous infusion of insulin, precision dosing, and programmable delivery schedules.

In infusion therapy, insulin doses are typically administered at a basal rate and in a bolus dose. When insulin is administered at a basal rate, insulin is delivered continuously over 24 hours in order to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates. Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life. For example, many of the T2D patients who are prescribed insulin therapy can be expected to convert from injections to infusion therapy due to an unmet clinical need for improved control. That is, a significant number of the T2D patients who take multiple-daily-injections (MDI) are not achieving target glucose control or not adhering sufficiently to their prescribed insulin therapy.

Typically, regardless of whether a diabetic patient uses multiple direct injections (MDIs) or a pump, the diabetic patient takes fasting blood glucose medication (FBGM) upon awakening from sleep, and also tests for glucose in the blood during or after each meal to determine whether a correction dose is required. In addition, the diabetic patient may test for glucose in the blood prior to sleeping to determine whether a correction dose is required, for instance, after eating a snack before sleeping.

To facilitate infusion therapy, there are generally two types of insulin pumps, namely, conventional pumps and patch pumps. Conventional pumps require the use of a disposable component, typically referred to as an infusion set, tubing set or pump set, which conveys the insulin from a reservoir within the pump into the skin of the user. The infusion set consists of a pump connector, a length of tubing, and a hub or base from which a cannula, in the form of a hollow metal infusion needle or flexible plastic catheter, extends. The base typically has an adhesive that retains the base on the skin surface during use. The cannula can be inserted into the skin manually or with the aid of a manual or automatic insertion device. The insertion device may be a separate unit required by the user.

Another type of insulin pump is a patch pump. Unlike a conventional infusion pump and infusion set combination, a patch pump is an integrated device that combines most or all of the fluidic components, including the fluid reservoir, pumping mechanism and mechanism for automatically inserting the cannula, in a single housing which is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained. Such devices are replaced on a frequent basis, such as every three days, when the insulin reservoir is exhausted or complications may otherwise occur, such as restriction in the cannula or the infusion site.

Medical devices, such as patch pumps, which can be activated by a user to infuse potentially harmful substances, need to have a means to distinguish between valid or intentional user activation of controls and inadvertent activation of controls. Conventional devices provide several means of preventing inadvertent activation, ranging from electrically interlinked buttons to physical structures which prevent the accidental activation of controls.

However, conventional controls rely on complicated mechanical structure for activation buttons or switches to prevent accidental activation. Other conventional controls rely on, for example a two-button activation where the two buttons or switches are electrically interlinked and require precise manipulation to achieve activation.

Accordingly, there is a need for a user-activated fluid delivery system that provides protection from inadvertent activation by the user, while avoiding complicated mechanical structures for activation buttons and/or electrical interconnection of activation buttons or switches requiring precisely ordered or simultaneous activation.

SUMMARY OF THE INVENTION

An object of the present invention is to substantially address the above and other concerns, and provide a medical device for infusing medical substances which distinguishes between intentional and inadvertent activation of controls by employing a microprocessor to analyze the timing of activation signals from user controls.

Another object of the present invention is to provide a computer implemented signal processing algorithm to facilitate analysis of signals received from multiple activation switches associated with a medical device to prevent inadvertent activation of the medical device.

Another object of the present invention is to provide a medical device for infusing medical substances with easily accessible activation controls, such as activation buttons, that can be conveniently manipulated by a user without causing inadvertent infusion of a medical substance.

Another object of the present invention is to provide activation controls, such as activation buttons for a medical device for infusing medical substances, having a discernable tactile feel to a user, while ensuring that unintentional manipulation of such controls does not cause inadvertent infusion of a medical substance.

In accordance with an aspect of illustrative embodiments of the present invention, a medical device for infusing of medical substances comprises an interface for initiating at least two independent time traces based on user input; and a controller evaluating said time traces to command infusing of medical substance based on a conditional relationship between said time traces.

In accordance with an aspect of illustrative embodiments of the present invention, the user input can comprise a first user input and a second user input, and the at least two independent time traces comprise a first time trace and a second time trace. The user interface comprises a first user accessible activation control receiving the first user input and a second user accessible activation control receiving the second user input. The interface selectively initiates the first time trace based on the first activation control receiving the first user input, and selectively initiates the second time trace based on the second activation control receiving the second user input.

In accordance with an aspect of illustrative embodiments of the present invention, the conditional relationship depends on at least one the first start time, the first stop time, a first duration, the second start time, the second stop time, and a second duration.

In accordance with an aspect of illustrative embodiments of the present invention, the device can employs overlap of respective time traces initiated by activation of the activation buttons to determine whether activation is intended and valid. These time traces do not have to be initiated simultaneously or in any particular sequence.

In accordance with an aspect of illustrative embodiments of the present invention, the activation buttons can be elastomeric overmolded buttons set within cutouts in the housing, and, when depressed, make physical contact with respective switches.

The present invention may comprise a method or apparatus for operating a device with activation button(s) having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The above and/or other aspects and advantages of embodiments of the invention will be more readily appreciated from the following detailed description, taken in conjunction with the accompanying drawings, in which:

FIG. 24 is a cross-section of the device of FIG. 16 wherein the activation buttons are activated according to an illustrative implementation of the present invention.

Throughout the drawing figures, like reference numbers will be understood to refer to like elements, features and structures.

DETAILED DESCRIPTION OF THE ILLUSTRATIVE EMBODIMENTS

Figure 1:
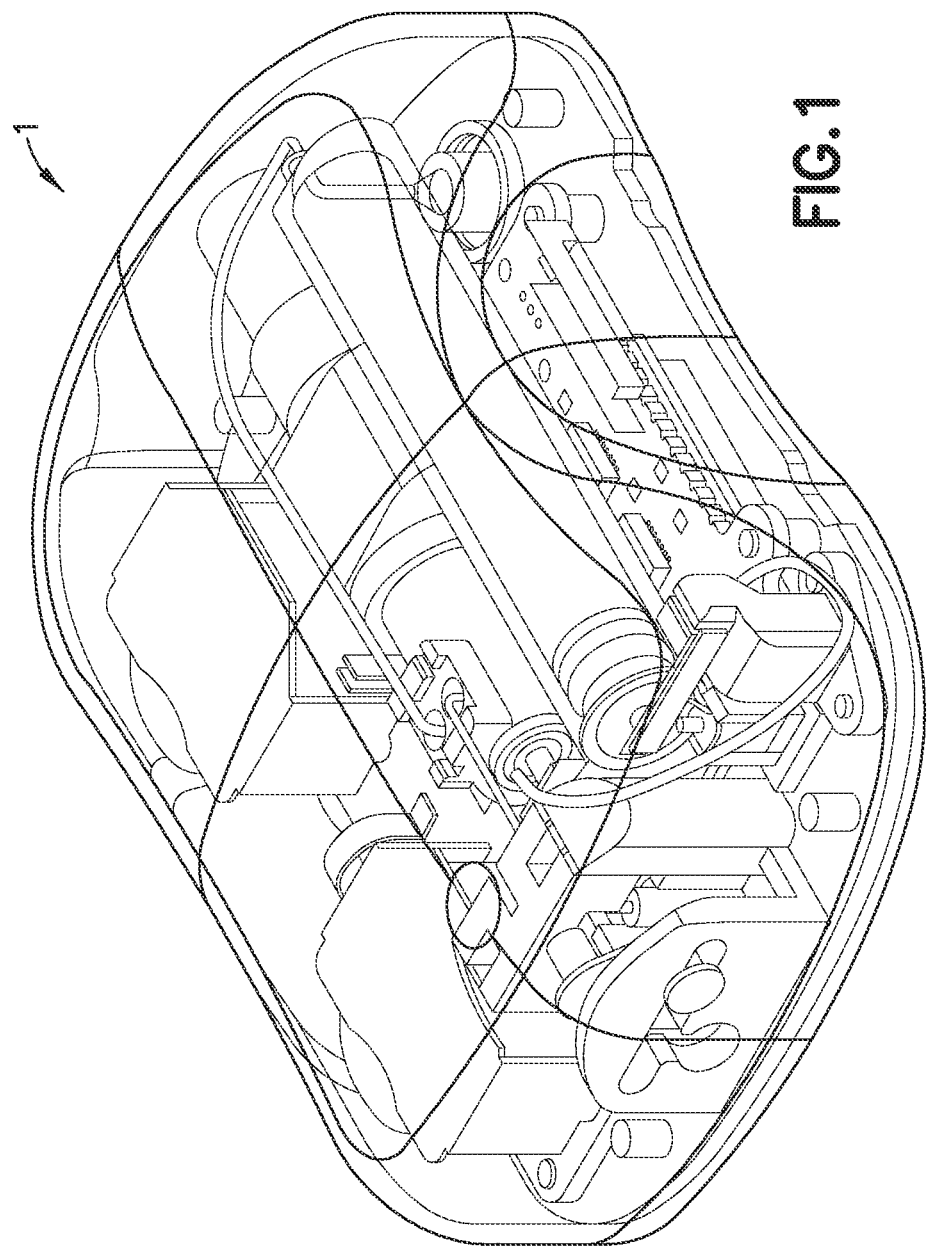
FIG. 1 is a perspective view of a patch pump according to an illustrative embodiment of the present invention.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative and are employed to aid illustration, but are not limiting.

Likewise, it will be understood by one skilled in the art that, unless otherwise explicitly stated in the detailed description that follows, relative and/or specific dimensions of various parts and components shown in the drawing figures are non-limiting examples provided to facilitate understanding of various illustrative implementations of the embodiments of the present invention While the illustrative embodiments are described with reference to diabetes management using insulin therapy, it is to be understood that these illustrative embodiments can be used with different drug therapies and regimens to treat other physiological conditions than diabetes using different medicaments than insulin.

Figure 2:
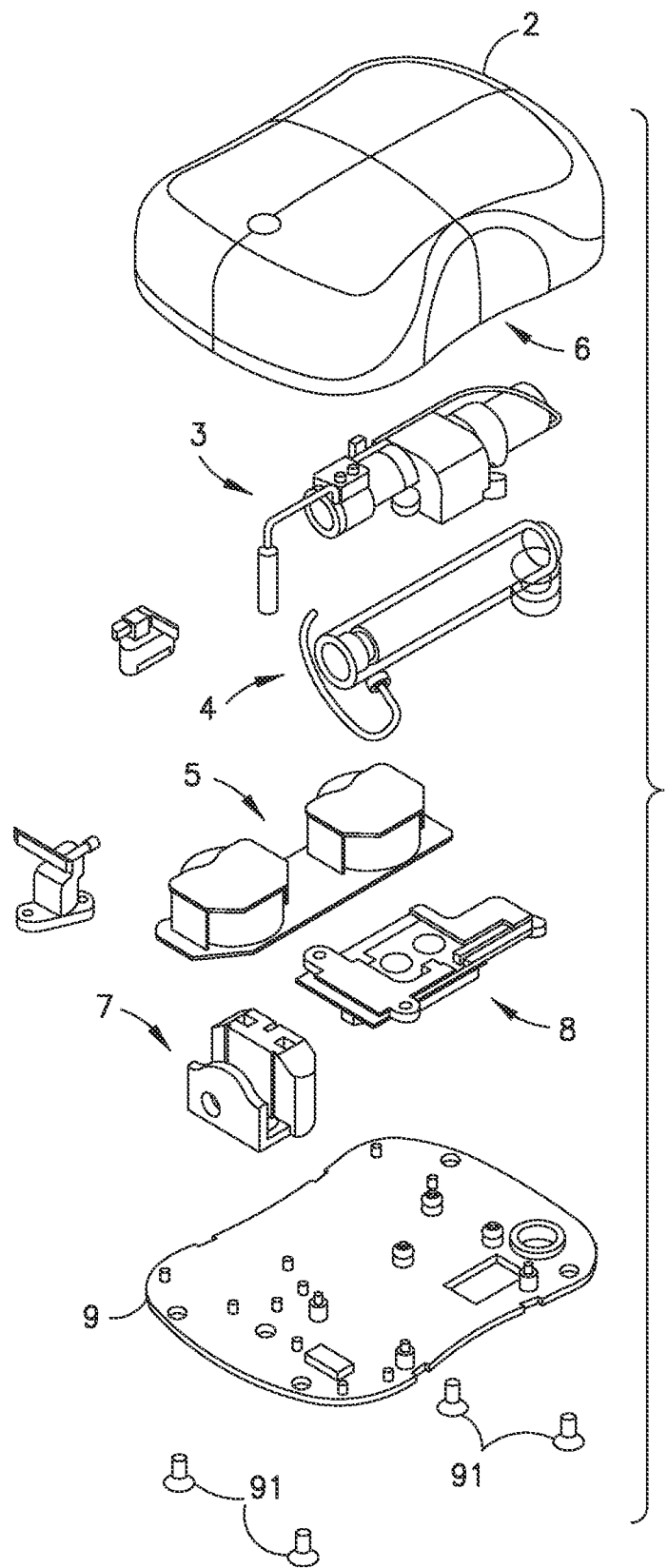
FIG. 2 is an exploded view of the various components of the patch pump of FIG. 1 according to an illustrative implementation of the present invention.

FIG. 1 is a perspective view of an illustrative embodiment of a medicine delivery device comprising a patch pump 1 according to an illustrative embodiment of the invention. The patch pump 1 is illustrated with a see-through cover for clarity and illustrates various components that are assembled to form the patch pump 1. FIG. 2 is an exploded view of the various components of the patch pump of FIG. 1, illustrated with a solid cover 2. The various components of the patch pump 1 may include: a reservoir 4 for storing insulin; a pump 3 for pumping insulin out of the reservoir 4; a power source 5 in the form of one or more batteries; an insertion mechanism 7 for inserting an inserter needle with a catheter into a user's skin; control electronics 8 in the form of a circuit board with optional communications capabilities to outside devices such as a remote controller and computer, including a smart phone; a pair of dose buttons 6 on the cover 2 (e.g., one button per side) for actuating an insulin dose, including a bolus dose; and a base 9 to which various components above may be attached via fasteners 91. The patch pump 1 also includes various fluid connector lines that transfer insulin pumped out of the reservoir 4 to the infusion site.

Figure 3:
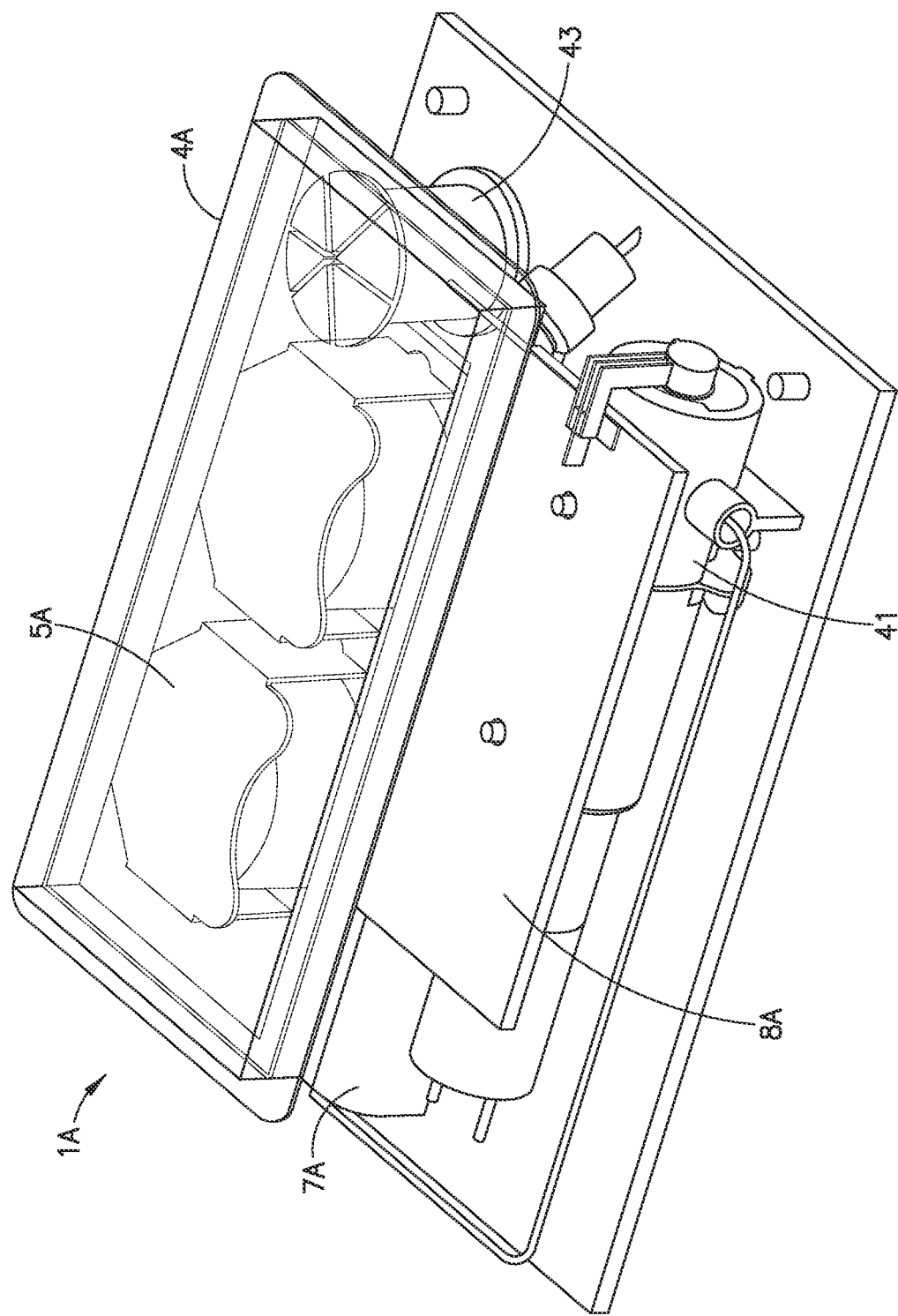
FIG. 3 is a perspective view of an alternative design for a patch pump having a flexible reservoir according to an illustrative implementation of the present invention.

FIG. 3 is a perspective view of an alternative design for a patch pump 1A having a flexible reservoir 4A, and illustrated without a cover. Such arrangement may further reduce the external dimensions of the patch pump 1A, with the flexible reservoir 4A filling voids within the patch pump 1A. The patch pump 1A is illustrated with a conventional cannula insertion device 7A that inserts the cannula, typically at an acute angle, less than 90 degrees, at the surface of a user's skin. The patch pump 1A further comprises: a power source 5A in the form of batteries; a metering sub-system 41 that monitors the volume of insulin and includes a low volume detecting ability; control electronics 8A for controlling the components of the device; and a reservoir fill port 43 for receiving a refill syringe (e.g., syringe 45 in FIG. 4) to fill the reservoir 4A.

Figure 4:
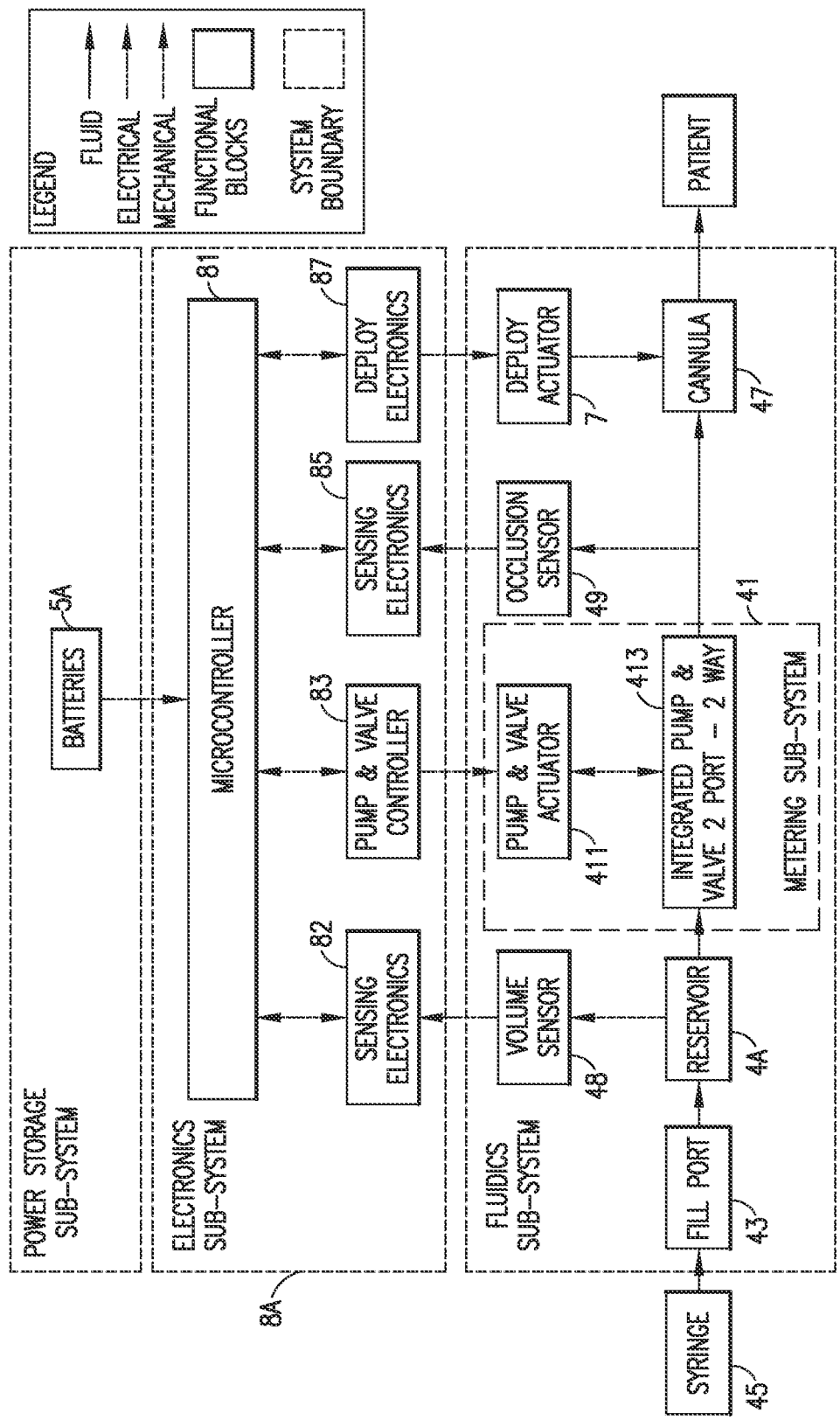
FIG. 4 is a block diagram depicting an illustrative implementation of a patch pump fluidic architecture and metering sub-system of the patch pump of FIG. 3.

FIG. 4 is an example patch pump fluidic architecture and metering sub-system diagram of the patch pump 1A of FIG. 3. The power storage sub-system for the patch pump 1A includes batteries 5A. The control electronics 8A of the patch pump 1A may include a microcontroller 81, sensing electronics 82, pump and valve controller 83, sensing electronics 85, and deployment electronics 87, that control the actuation of the patch pump 1A. The patch pump 1A includes a fluidics sub-system that may include a reservoir 4A, volume sensor 48 for the reservoir 4A, a reservoir fill port 43 for receiving a refill syringe 45 to refill the reservoir 4A. The fluidics sub-system may include a metering system 41 comprising a pump and valve actuator 411 and an integrated pump and valve mechanism 413. The fluidics sub-system may further include an occlusion sensor 49, a deploy actuator 7, as well as the cannula 47 for insertion into an infusion site on the user's skin. The architecture for the patch pumps of FIGS. 1 and 2 can be the same or similar to that which is illustrated in FIG. 4.

Figure 5:
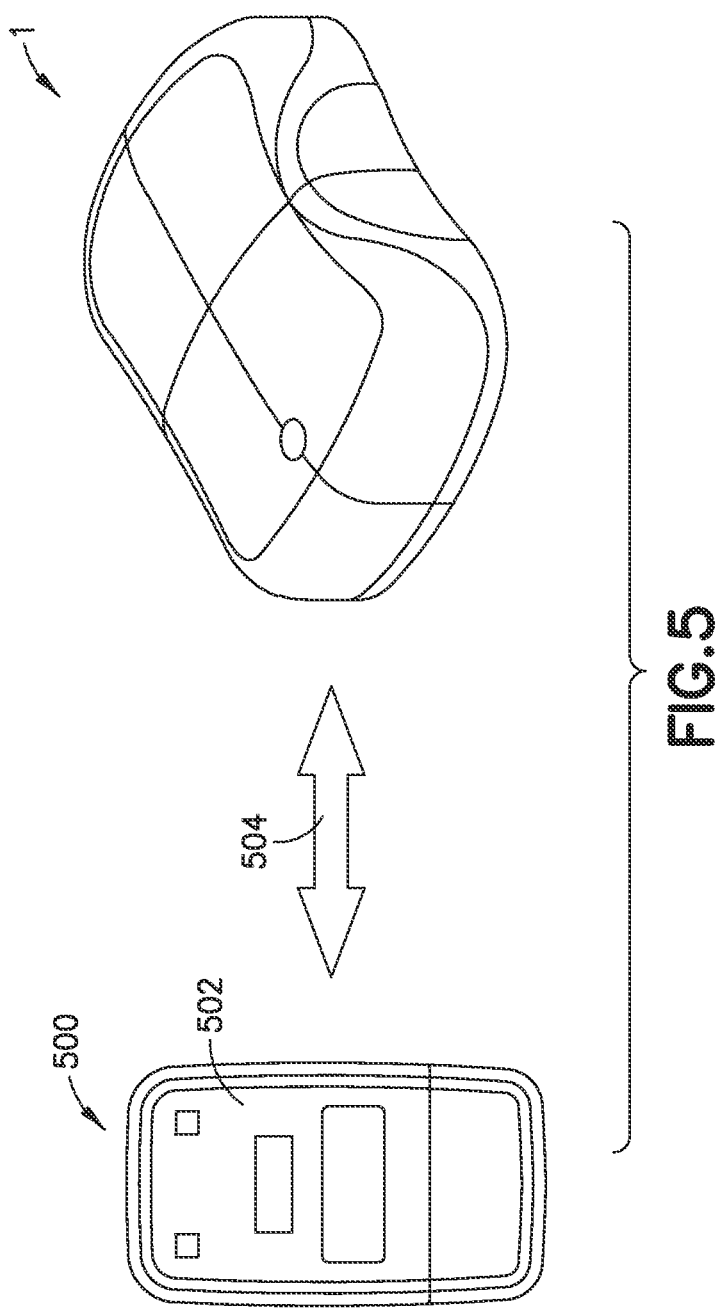
FIG. 5 depicts an illustrative embodiment of the present invention including a wireless remote controller for controlling the operation of a medicine delivery device such as, for example, a patch pump.

FIG. 5 illustrates a wearable medical delivery device (e.g., insulin delivery device (IDD) such as patch pump 1) operable in conjunction with a remote wireless controller (WC) 500 that communicates with the pump 1. The WC can comprise a graphical user interface (GUI) display 502 for providing a user visual information about the operation of the patch pump 1 such as, for example, configuration settings, an indication when a wireless connection to the patch pump is successful, and an indication when a dose is being delivered, among other display operations. In an illustrative implementation, the GUI display 502 can include a touchscreen display functionality programmed to allow a user to provide touch inputs such as a swipe to unlock, swipe to confirm a request to deliver a bolus, and selection of confirmation or settings buttons, among other user interface operations.

The WC can communicate with the delivery device (e.g., patch pump 1) using any one or more of a number of communication interfaces 504. For example, a near field radiation interface can be provided to synchronize the timing of the WC and patch pump 1 and otherwise facilitate pairing upon start up. Another interface can be provided for wireless communication between the WC and the patch pump 1 that employs a standard BlueTooth Low Energy (BLE) layer, as well as Transport and Application layers. Non-limiting examples of Application layer commands include priming, delivering basal dose, delivering bolus dose, cancelling insulin delivery, checking patch pump 1 status, deactivating the patch pump 1, and patch pump 1 status or information reply.

Figure 6:
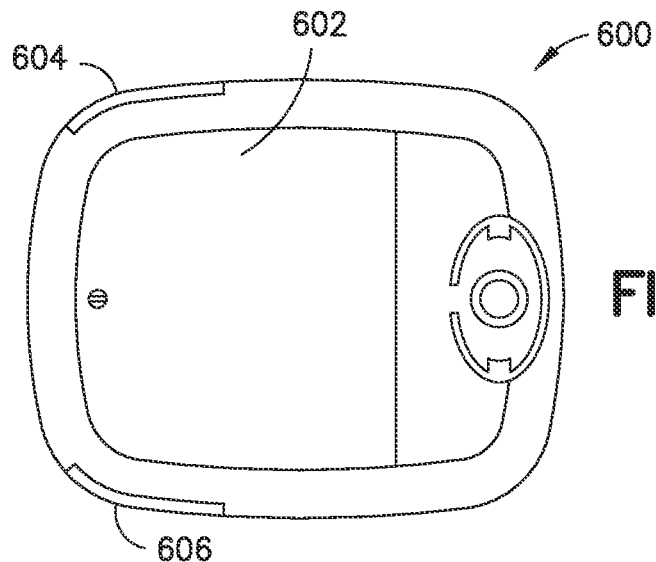
FIG. 6 is a top view of an outer housing of a device (e.g., a medicine delivery device such as a patch pump) according to an illustrative embodiment of the present invention.

FIG. 6 is a top view of an outer housing 602 of a medicine delivery device comprising a patch pump 600 according to an illustrative embodiment of the invention, including two push buttons 604, 606 accessible to a user for initiating delivery of medicine contained in the device. In an illustrative implementation where the WC is employed, certain predetermined manipulation of buttons 604, 606 can be used to synchronize communication and facilitate pairing between medicine delivery device and the WC.

Figure 7A:
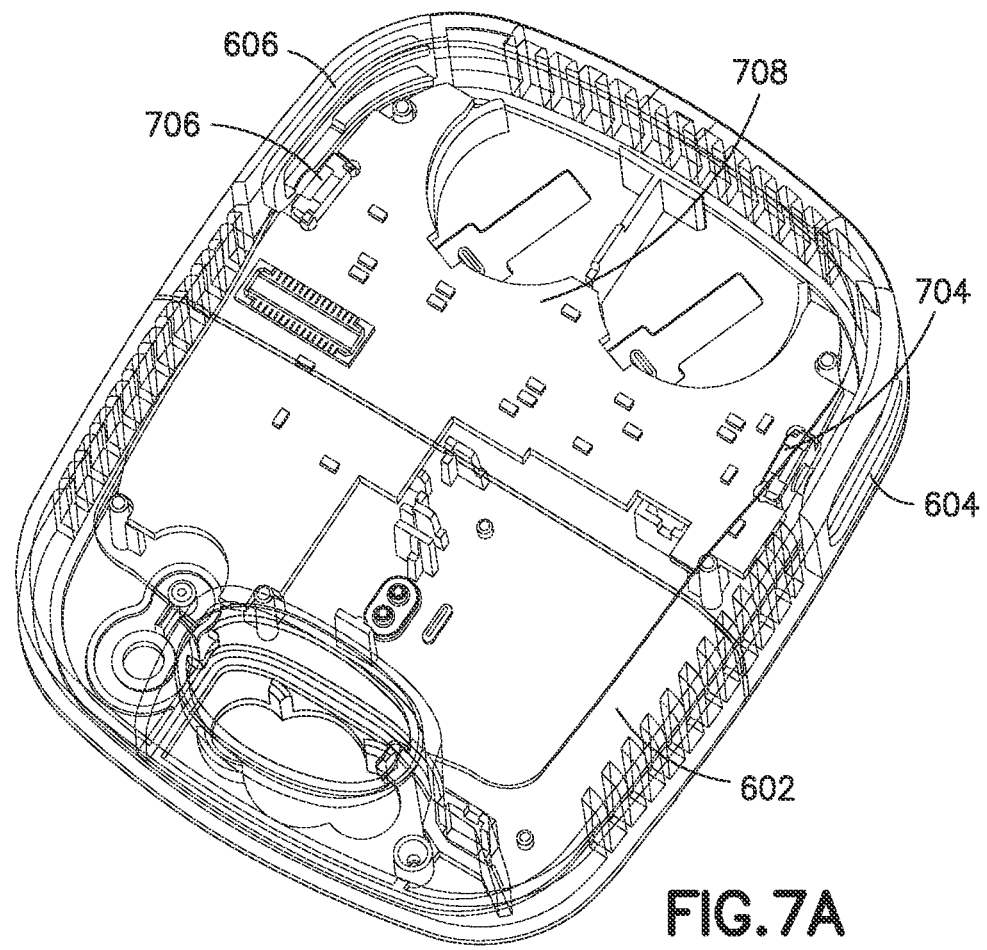
FIG. 7A is a perspective view of the device of FIG. 6 according to an illustrative embodiment of the present invention showing electrical switches mounted on a printed circuit board according to an illustrative implementation of the present invention.
Figure 14A:
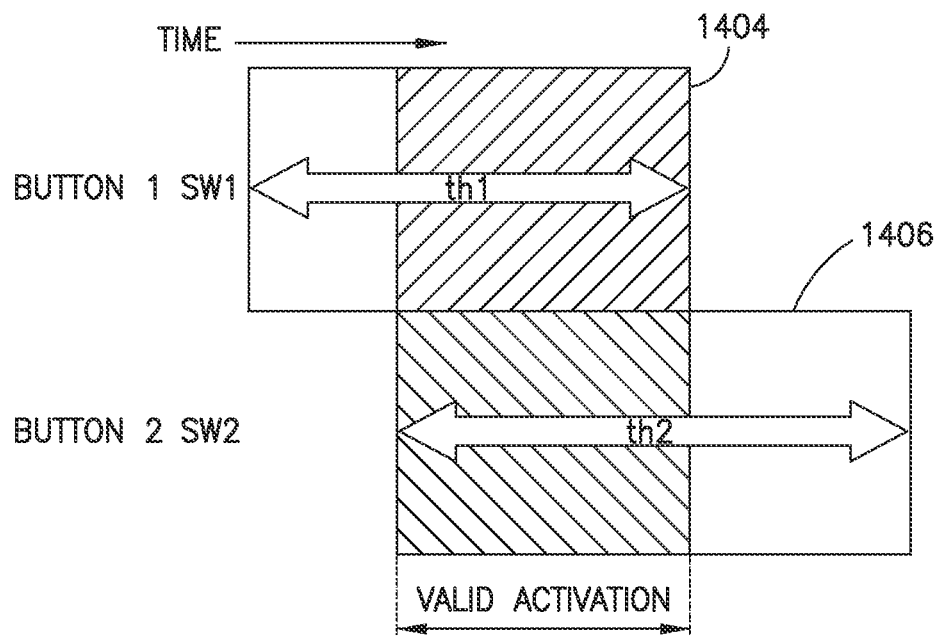
FIGS. 14A, 14B and 14C are conceptual timing diagrams depicting activation validity verification via time analysis according to illustrative implementations of the present invention.
Figure 14B:
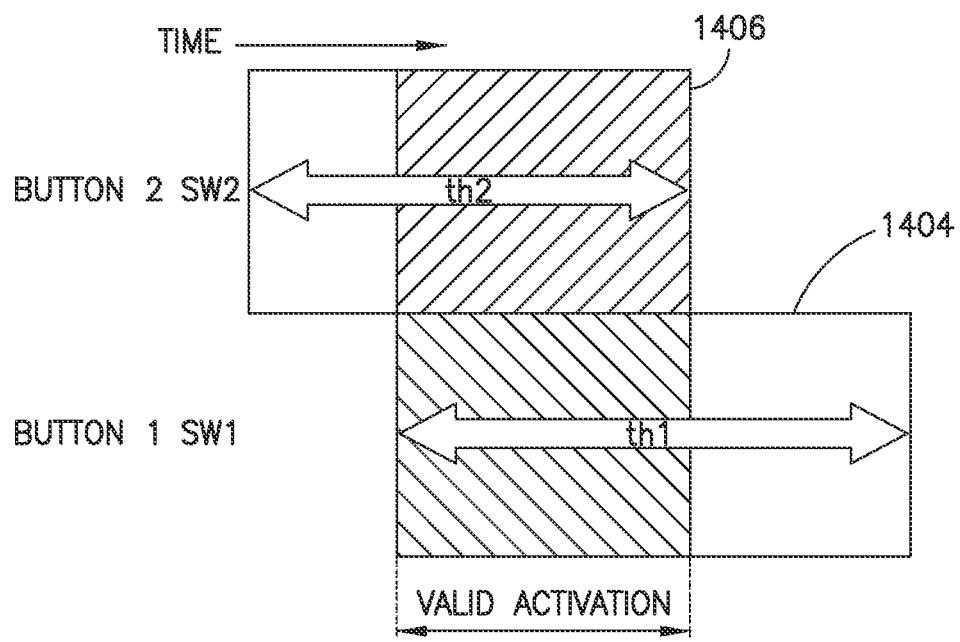
Figure 14C:
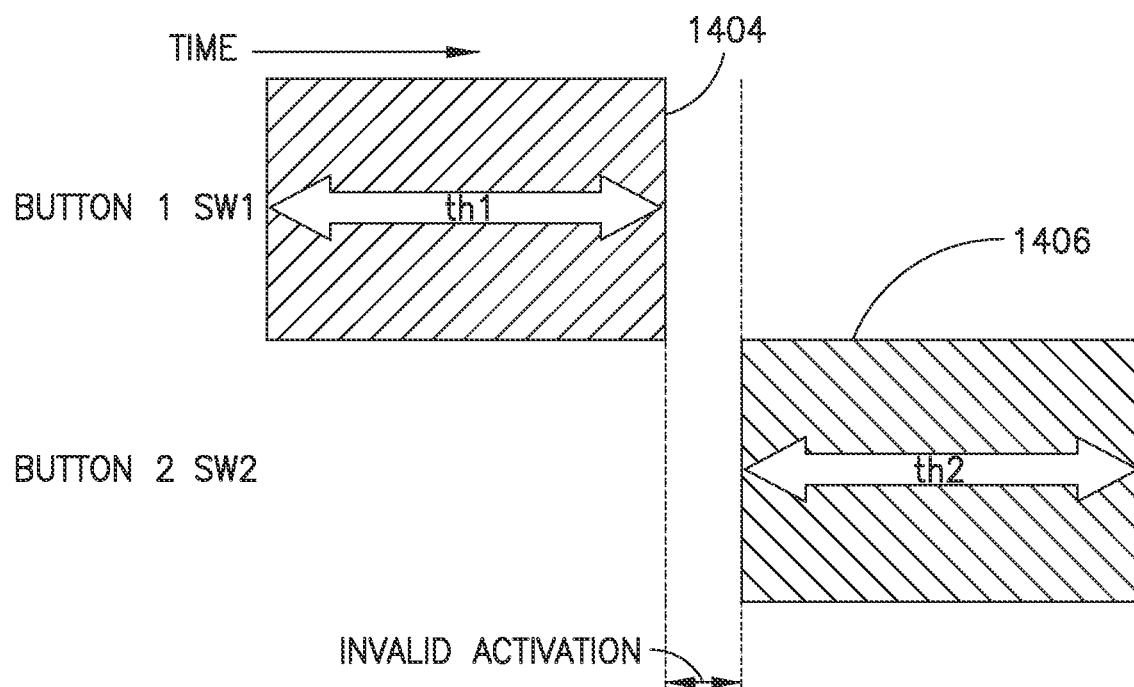
Figure 15:
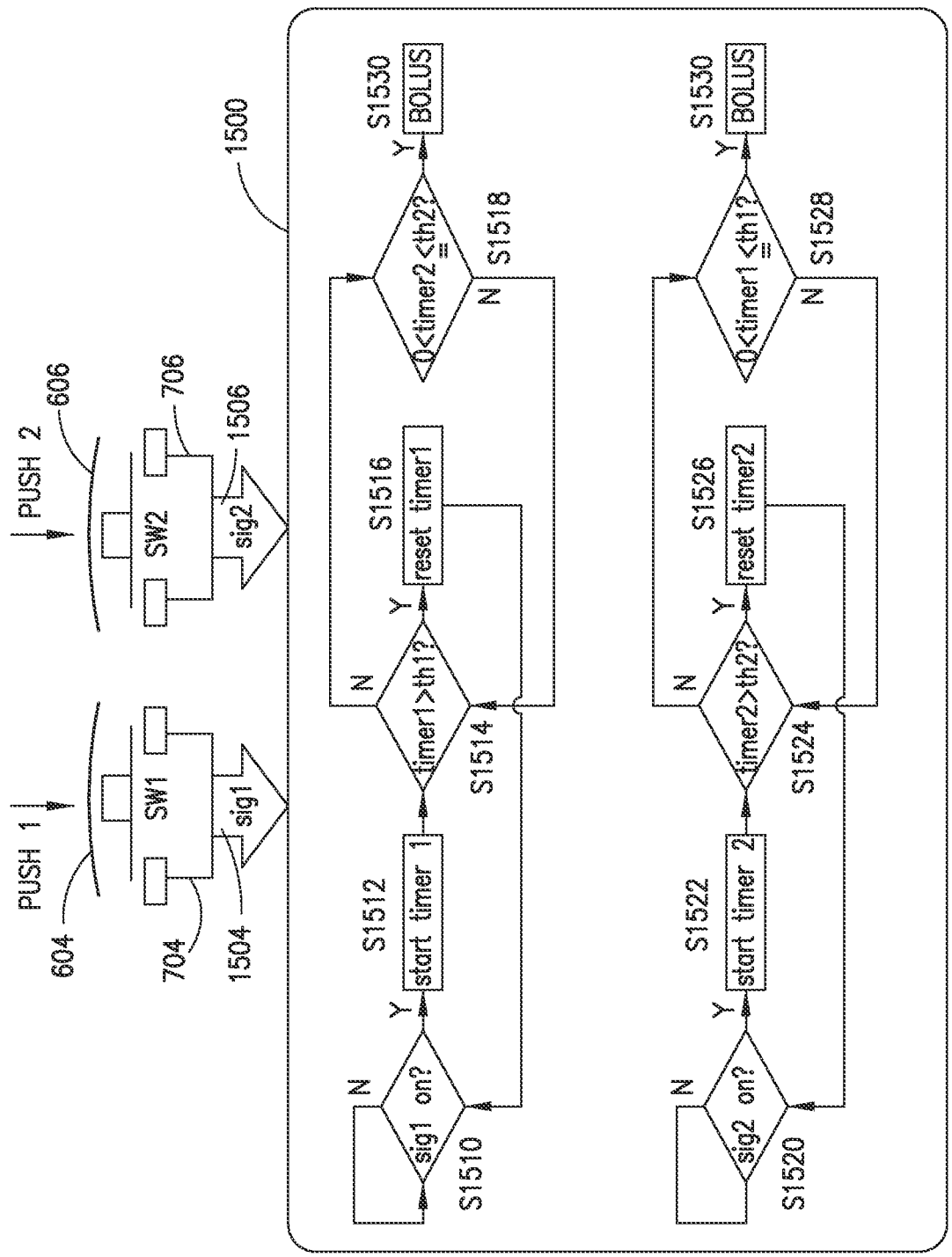
FIG. 15 is a process flow diagram depicting an example of signal processing according to an illustrative embodiment of the present invention.
Figure 16:
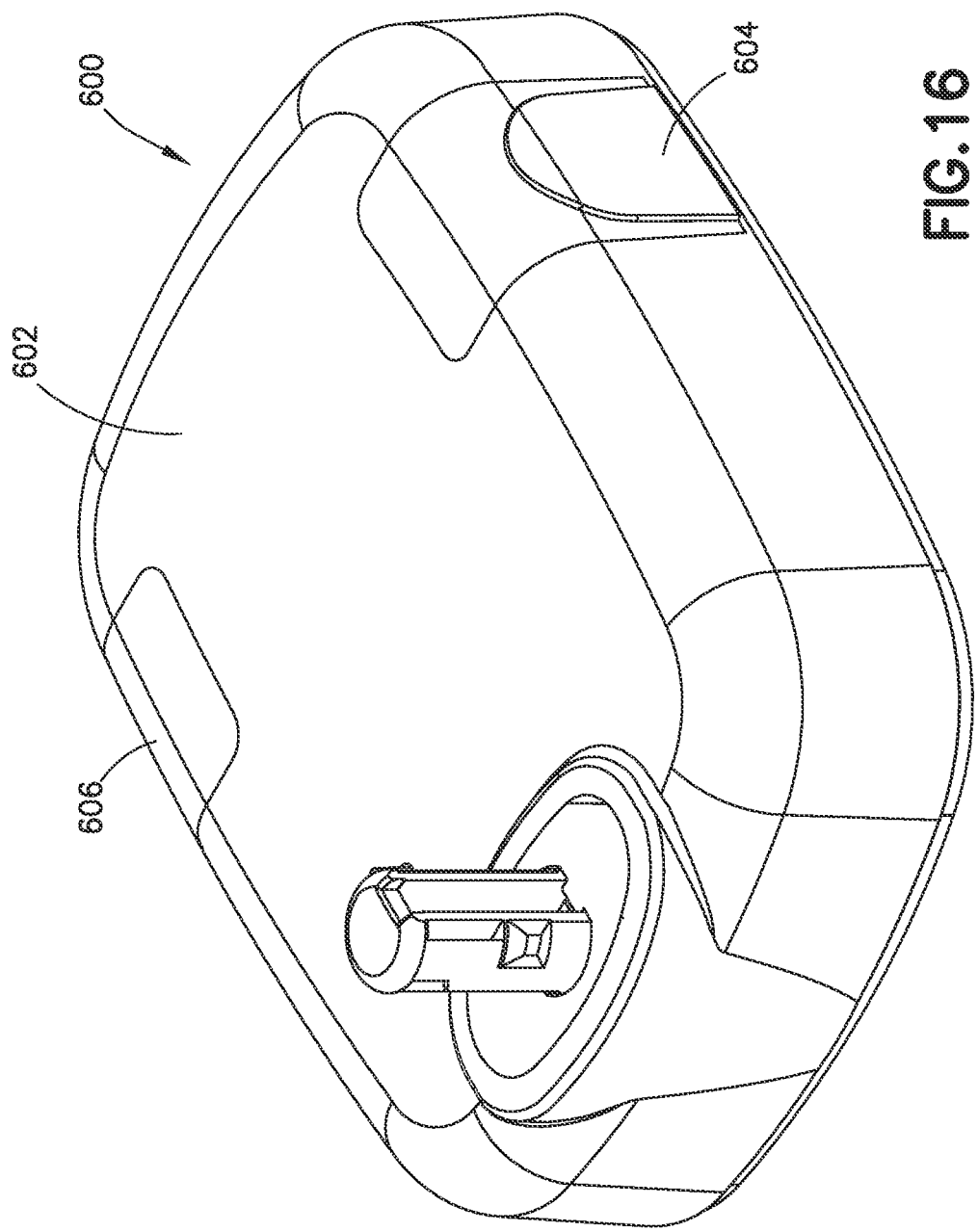
FIG. 16 is perspective view of an outer housing of a device (e.g., a medicine delivery device such as a patch pump) according to an illustrative embodiment of the present invention.

As further illustrated in FIG. 7A, in an illustrative implementation of medicine delivery device comprising a patch pump 600, initiation of medicine delivery (e.g., "bolus") can be performed by operation of buttons 604, 606 (for example, a user depressing one or both buttons) to cause respective (e.g., electrical) switches 704, 706 to output respective activation signals to a controller 1500 (e.g., signal processing as illustrated in FIG. 15) which can be disposed within the housing 602. In order to distinguish between valid or user intended activation and inadvertent activation of switches 704, 706, the controller processes the activation signals (for example, utilizing a microprocessor such as microcontroller 81 in FIG. 4 and internal or external non-transient computer readable medium) and controls delivery of medicine based on results of the processing as described in more detail with reference to FIGS. 14A-14C and 15.

Referring to diagrams of FIGS. 14A-14C, according to illustrative embodiments of the present invention, timing of the activation signals can be used to verify whether a user intended to initiate delivery of medicine when causing the activation signals. In an illustrative implementation of the present invention for an infusion device with two buttons, such as devices whose features are illustrated in FIGS. 1 through 13B, as each button 1 and button 2 (such as button 604 and button 606) is pushed, a respective timer 1404 and 1406 can be activated by activation signals from respective switches SW1 and SW2 (such as switches 704 and 706) for a respective set amount of time (for example, th1 and th2, where th1 may or may not be equal to th2).

If the time-trace of each timer overlaps with one another, as illustrated in FIGS. 14A and 14B, a valid activation is registered. If one timer expires before the other is activated, as illustrated in the example of FIG. 14C, an invalid activation is registered. Similarly, a time activation of only one timer (for example, as a result of pushing only a respective one of the two buttons 604, 606) is registered as an invalid activation.

As will be appreciated by one skilled in the art, a timer can be implemented in hardware, for example as a timing circuit using discrete electrical components, or in software, for example as a counter using computer executable instructions. The usage of timers as a way to classify button pushes as valid or invalid could potentially mean fewer parts than a physical interlocking type of design, which would translate to lowered cost and assembly time.

Referring to FIG. 15, according to an illustrative embodiment of the present invention, a controller 1500, such as a programmable microprocessor, monitors outputs of switches SW1 and SW2, such as electrical switches 704 and 706, in order to control dispensing of medicine based on valid activation of buttons 604 and 606 as follows.

When a user operates ("push 1") button 604, switch (SW1) 704 outputs an activation signal (sig1) 1504, and when a user operates ("push 2") button 606, switch (SW2) 706 outputs an activation signal (sig2) 1506. Controller 1500 performs computer executable instructions including:

Determine (S1510) whether activation signal sig1 was received from switch SW1, and if activation signal sig1 was received from switch SW1, start timer1 (S1512). As will be appreciated by one skilled in the art, timer1 can be implemented in software as, for example, a counter1.

Determine (S1520) whether activation signal sig2 was received from switch SW2, and if activation signal sig2 was received from switch SW2, start timer2 (S1522). As will be appreciated by one skilled in the art, timer 2 can be implemented in software as, for example, a counter 2.

Determine (S1514) whether timer1 has timed out, for example by checking whether the timer1 is greater than a preset threshold value th1, and
- if timer1 is greater than th1, then timer1 has timed out: reset (S1516) timer1, for example, to zero,
- if timer1 is not greater than th1, then timer1 has not timed out:

determine (S1518) whether timer2 has been activated (by sig2) and has not timed out.

Determine (S1524) whether timer2 has timed out, for example by checking whether the timer2 is greater than a preset threshold value th2, and
- if timer2 is greater than th2, then timer2 has timed out: reset (S1526) timer2, for example, to zero,
- if timer2 is not greater than th2, then timer2 has not timed out: determine (S1528) whether timer1 has been activated (by sig1) and has not timed out.

If timer1 and timer2 have not timed out, i.e., time traces overlap, then activation is valid: dispense medicine (S1530).

Notably, the two signals 1504 and 1506 (e.g., sig1 and sig2) can be processed independently and/or in parallel with each other.

According to illustrative embodiments of the present invention as illustrated in the non-limiting examples of FIGS. 14A, 14B and 15, the determination whether an activation to dispense medicine is valid (e.g., intended by the device user) does not require buttons 1 and 2 to be pushed in a certain sequence or simultaneously. Instead, the determination whether an activation to dispense medicine is valid is based on an overlap of respective time traces initiated by respective activation signals caused by pushing respective buttons 1 and 2. These time traces do not have to be initiated simultaneously, or in any particular sequence, because the overlap is simply based on the two time traces being present together for a certain time period, i.e., the overlap, as illustrated in FIG. 14A. For example, FIG. 14A shows button 1 pushed before button 2; however, the same valid activation can be achieved by pushing button 2 before button 1, as shown in FIG. 14B.

The duration of the overlap constituting a valid activation can be preset, or for example, programmed in a non-transient computer readable memory internal or external to controller 1500. Likewise, the duration of activation signals, th1 and th2 can be preset, or for example, programmed in a non-transient computer readable memory internal or external to controller 1500, and can be independently set to different or same durations with respect to one another. Thus, according to an illustrative implementation of the present invention, the determination whether an activation to dispense medicine is valid can be based on the setting for the overlap, th1 and th2, which can be independently preset, programmed, or adjusted, for example in a non-transient computer readable memory internal or external to controller 1500. Programming of the button activation parameters such as the duration of the overlap, th1 and th2 can depend on any of a number of factors such as, for example, locations of the buttons on the device, user ergonomics and/or habits, and structural requirements of the medical delivery device. For example, the button activation parameters can depend on any one or more of: bounce associated with the contacts of the switches, human factor considerations (e.g., timing associated with typical user manipulation of the device), tactile feedback qualities of a particular mechanical button implementation, among other factors.

FIG. 7B through 13B illustrate illustrative implementations of various housing and push button ("bolus button") structures for medicine delivery devices or infusion devices according the present invention. These structures can be utilized independently of, or in conjunction with, the controller 1500 and the timing analysis according to illustrative embodiments of the present invention.

Illustrative implementations of the present inventions may address several functional requirements for a bolus button on an infusion device such as, for example, a button design which reliably registers valid pushes while minimizing inadvertent pushes, while also sealing against ingress to the interior of the infusion device.

Figure 7B:
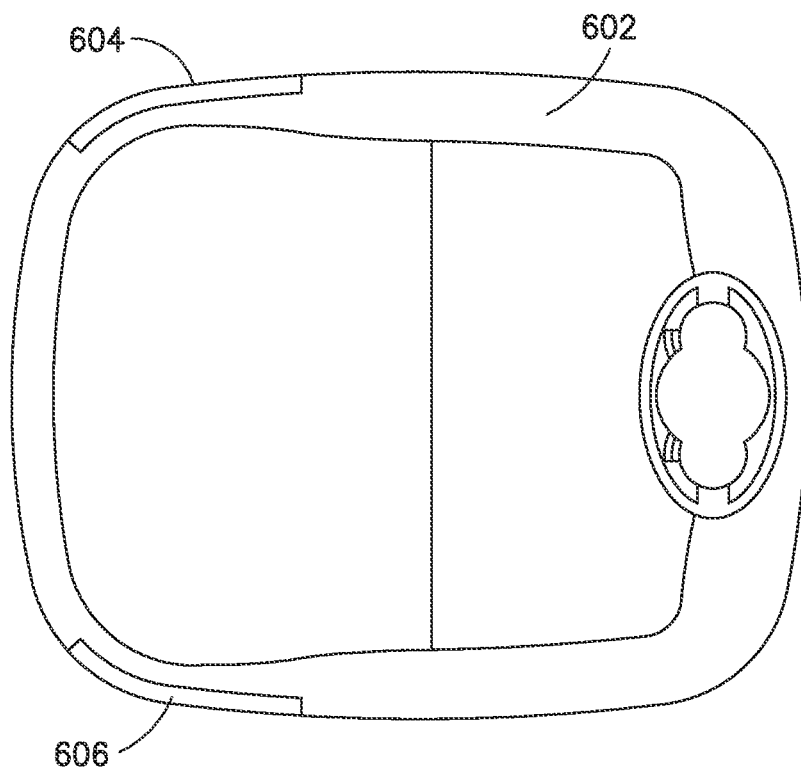
FIGS. 7B and 7C are top and side views, respectively, of an outer housing of the device of FIG. 6 according to an illustrative embodiment of the present invention.
Figure 7C:
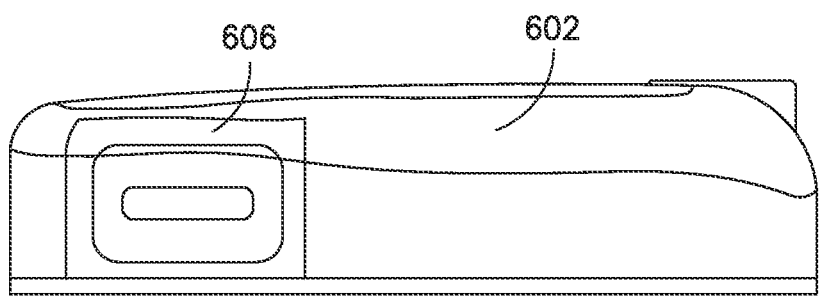

FIGS. 7B and 7C illustrate a top and side view of a housing of a medicine delivery device 600 according to an illustrative embodiment of the present invention including a rigid shell 602 and push buttons 604 and 606 with an overmolded elastomer to provide a seal and improved user grip. In this illustrative implementation, in order to activate electrical switches, which can be mounted on a printed circuit board 708, as illustrated in FIG. 7A, the user needs to push the buttons 604, 606 on the outer housing with a force of sufficient magnitude and travel to be applied to these switches for activation.

Figure 8:
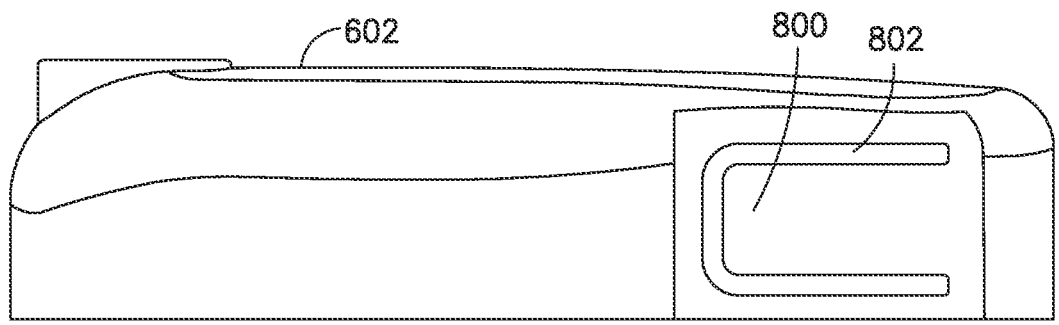
FIG. 8 is an exterior side view of the device of FIG. 6 depicting an implementation of an activation button for at least one of the electrical switches according to an illustrative embodiment of the present invention.
Figure 9:
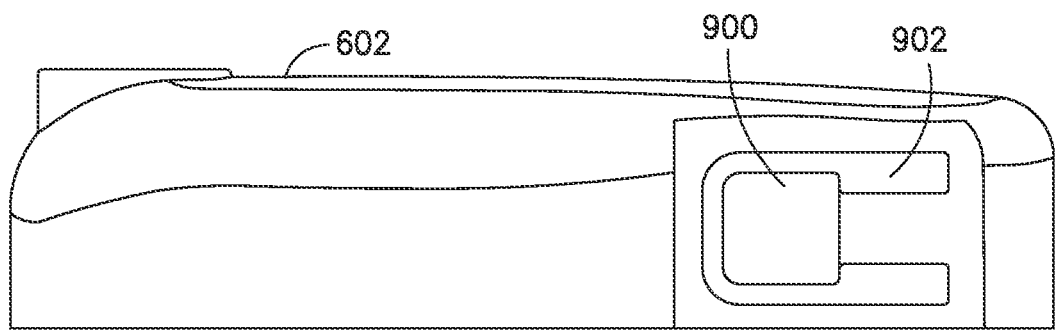
FIG. 9 is an exterior side view of the device of FIG. 6 depicting an implementation of an activation button for at least one of the electrical switches according to an illustrative embodiment of the present invention.
Figure 10A:
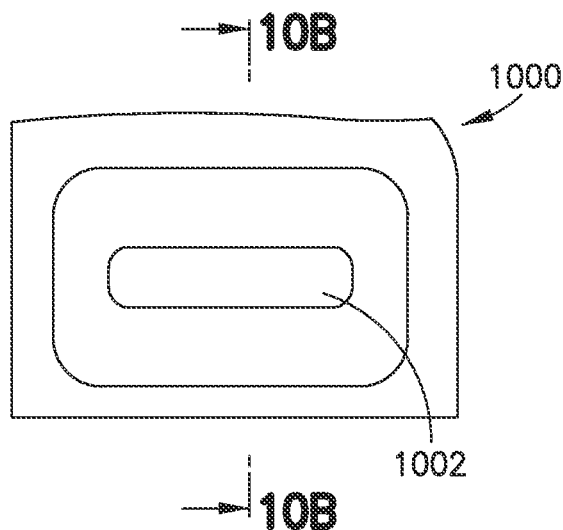
FIGS. 10A and 10B are partial top and cross-section views depicting another implementation of an activation button for at least one of the electrical switches according to an illustrative embodiment of the present invention.
Figure 10B:
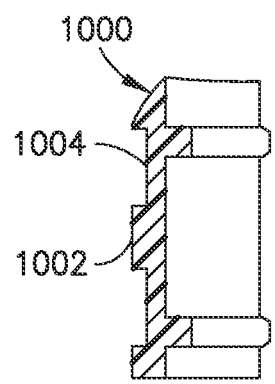
Figure 11A:
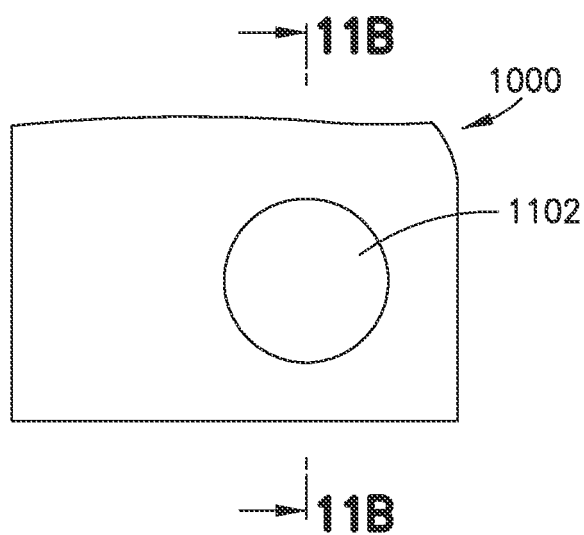
FIGS. 11A and 11B are partial top and cross-section views depicting another implementation of an activation button for at least one of the electrical switches according to an illustrative embodiment of the present invention.
Figure 11B:
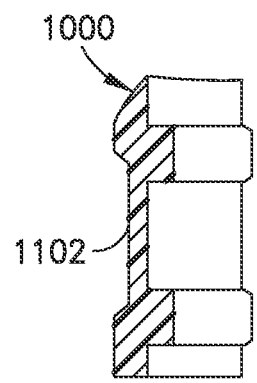
Figure 12A:
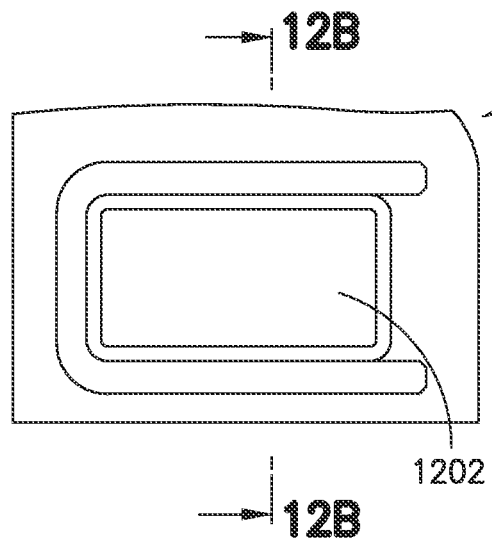
FIGS. 12A and 12B are partial top and cross-section views depicting another implementation of an activation button for at least one of the electrical switches according to an illustrative embodiment of the present invention.
Figure 12B:
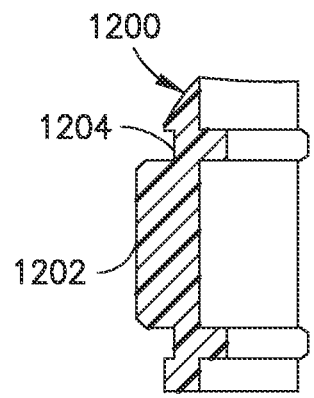
Figure 13A:
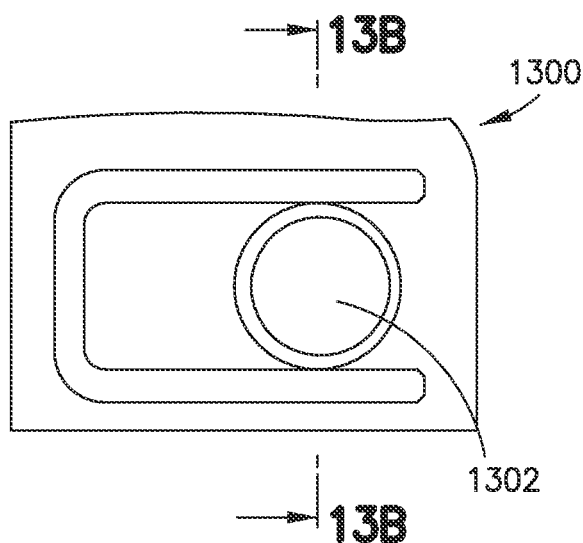
FIGS. 13A and 13B are partial top and cross-section views depicting another implementation of an activation button for at least one of the electrical switches according to an illustrative embodiment of the present invention.
Figure 13B:
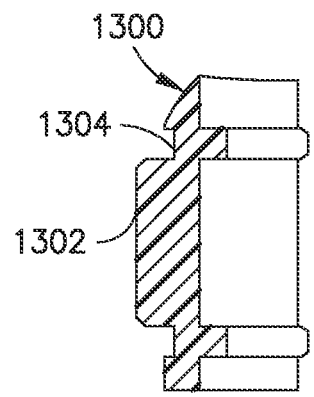

In an illustrative implementation a rigid flex arm can be provided under the overmolded button 604, 606 to enlarge the area which a user can push on the button and still create a sufficient activation force on the electrical switch. FIGS. 8 and 9 illustrate a side view of a housing 602 without the overmold to show examples of a flex arm according to embodiments of the present invention. In particular, FIG. 8 illustrates an example of a flex arm 800 with a smaller cutout 802 which would produce a stiffer flex arm 800. On the other hand, FIG. 9 illustrates an example of a more flexible flex arm 900 due to a larger cut out 902. The overall shape of the cutout 802 or 902 and the total cutout area can vary depending on the materials (e.g., material type, thickness, flexibility) used for the housing cover or shell 702 and overmolded elastomer, and the desired flexibility or stiffness or travel distance needed to activate the switch 704, 706 corresponding to the button 604, 606.

FIGS. 10A-13B illustrate side and cross section (along respective lines A-A, B-B, C-C, D-D) views of an elastomeric overmold according to illustrative embodiments of the present invention. In illustrative implementations of the present invention, such overmold is intended to provide a seal against foreign substances from entering the interior of the housing of a medicine delivery device. It is also an interface for the user to interact with the device (for example to activate switches 704, 706 as described above with reference to FIG. 7A). The illustrative implementations of an elastomeric overmold according to the present invention shown in FIGS. 10A-13B can emphasize or deemphasize certain characteristics of this interface.

Illustrative implementations of an elastomeric overmold according to the present invention as illustrated in FIGS. 10A-10B and 11A-11B provide designs 1000 and 1100, respectively, which have features 1002 and 1102, respectively, that would not protrude from, or be flush with, the outer body, which provides a lesser chance of inadvertent activation.

Illustrative implementations of an elastomeric overmold according to the present invention as illustrated in FIGS. 12A-12B and 13A-13B provide designs 1200 and 1300, respectively, which have features 1202 and 1302, respectively, that would protrude from the main surface of the housing. Such an illustrative implementation may provide a positional tactile cue for the user, which may be particularly useful if the user does not have a line of sight to the device (e.g., the user is wearing the patch pump 600 adhered to the skin of the abdomen and under clothing).

An additional feature of illustrative implementations of an elastomeric overmold according to the present invention as illustrated in FIGS. 10A-10B, 12A-12B and 13A-13B is a groove 1004, 1204 and 1304, respectively, around a portion of the button which reduces the cross section of the elastomer, which would in turn lower the force needed to flex the button.

According to illustrative embodiments of the present invention, an elastomeric overmold design, as illustrated in FIGS. 7A-13B has an advantage of being a system of designs tunable for the desired forces and feel. For example, a lower force combination would be the large cutout flex arm, as illustrated in FIG. 9 coupled with the indented rectangle of FIGS. 10A-10B.

The housing cover or shell 602 or button 604, 606 can have an interior (i.e., relative to the contents of the housing 602) surface area or interior attribute (e.g., ridge or rib such as rib 612 in FIG. 17) that is disposed directly opposite and apart from the corresponding switch 704, 706 when the button 604, 606 is not depressed, and that comes into contact (e.g., physical contact) with the switch 704, 706 when the button 604, 606 is depressed. The buttons 604, 606 can be mounted on or formed with the housing 700 in such a manner that depression of a button 604 or 606 causes the corresponding interior surface area or attribute to translate, move or otherwise extend toward the corresponding switch 704, 706.

Figure 17:
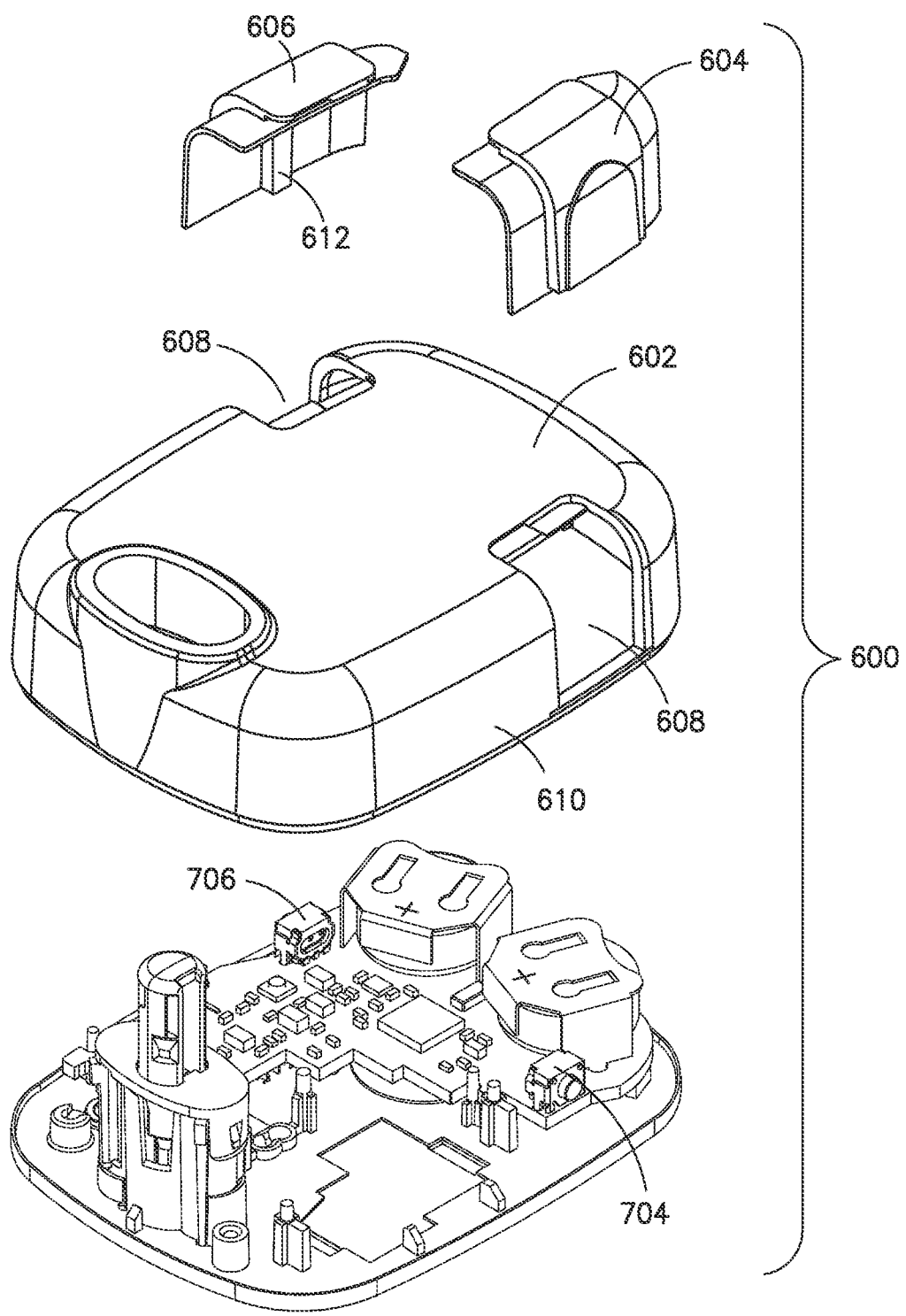
FIG. 17 is an exploded view of the various components of the device of FIG. 16 according to an illustrative implementation of the present invention.
Figure 18:
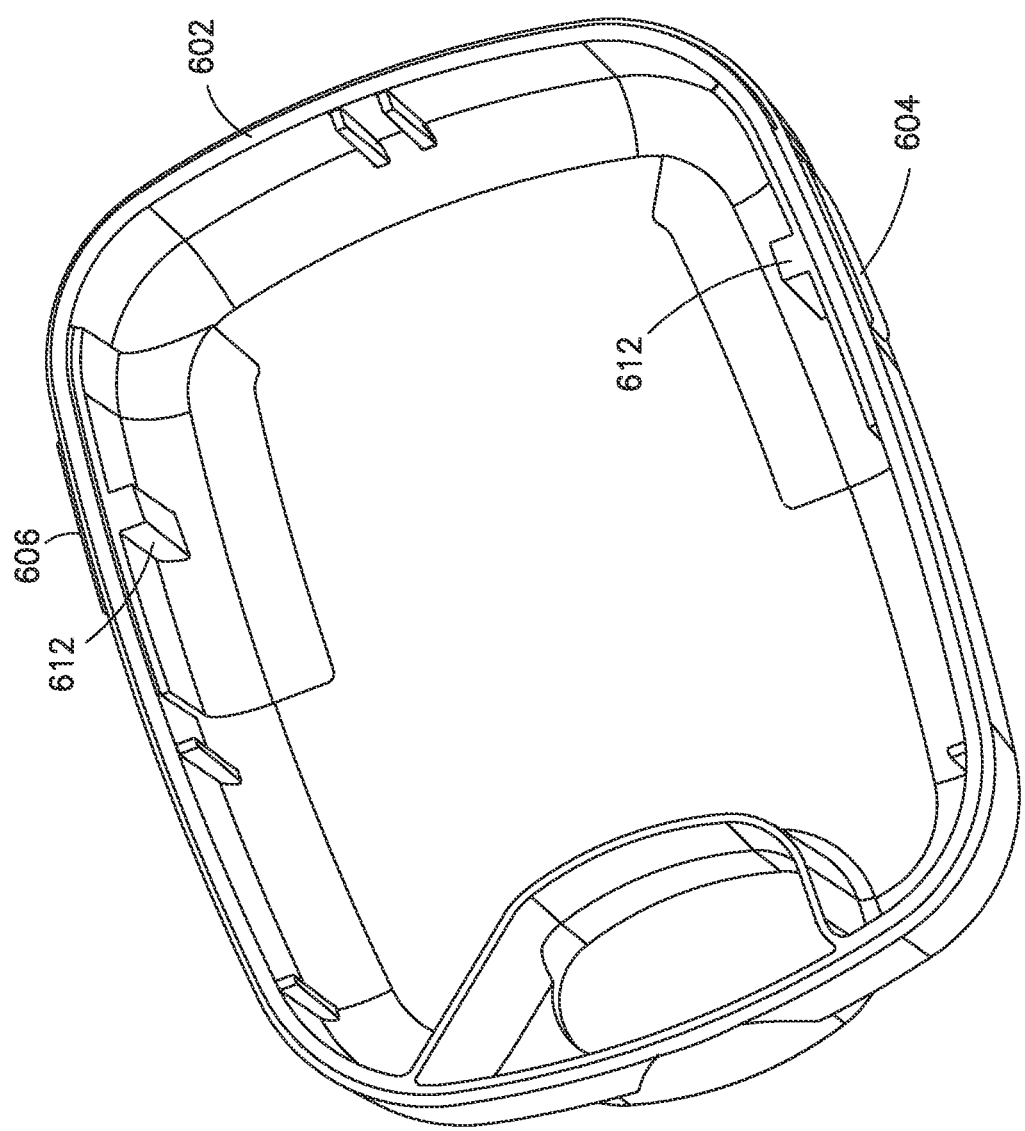
FIG. 18 is a bottom view of the outer housing of the device of FIG. 16 according to an illustrative implementation of the present invention.
Figure 19:
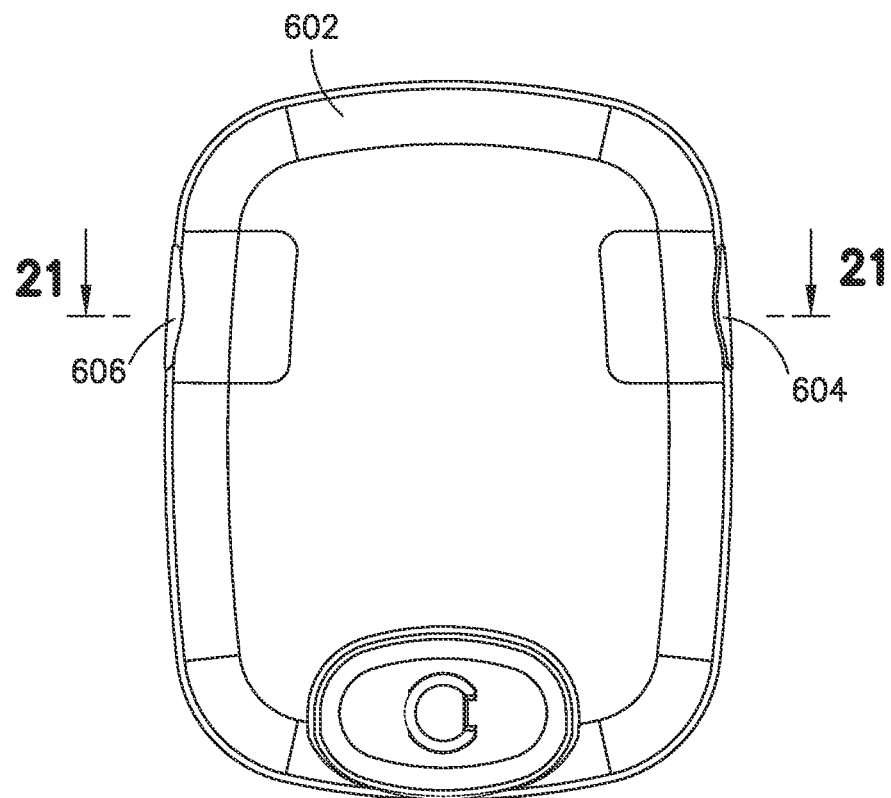
FIG. 19 is a top view of the device of FIG. 16 wherein the activation buttons are not activated according to an illustrative implementation of the present invention.
Figure 20:
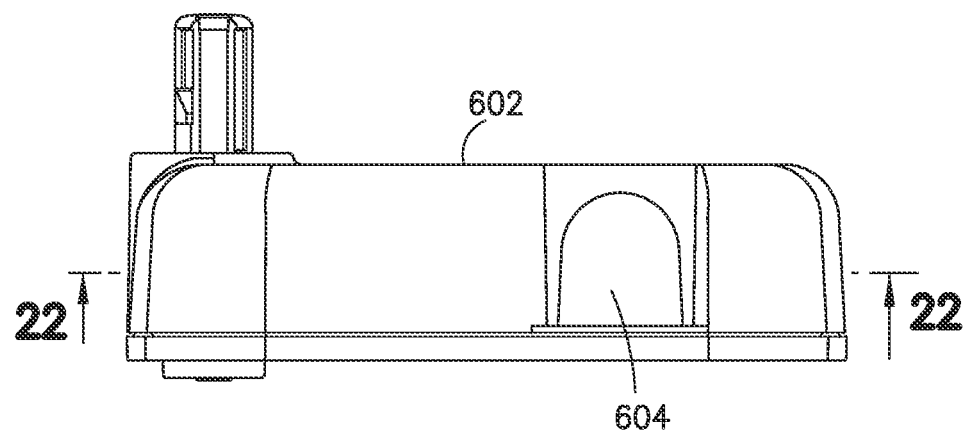
FIG. 20 is a side view of the device of FIG. 16 wherein the activation buttons are not activated according to an illustrative implementation of the present invention.
Figure 21:
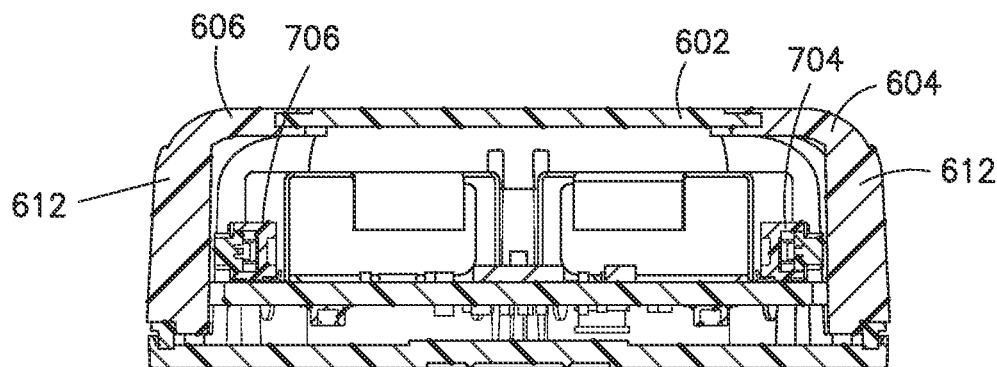
FIG. 21 is a cross-section of the device of FIG. 19 wherein the activation buttons are not activated according to an illustrative implementation of the present invention.
Figure 22:
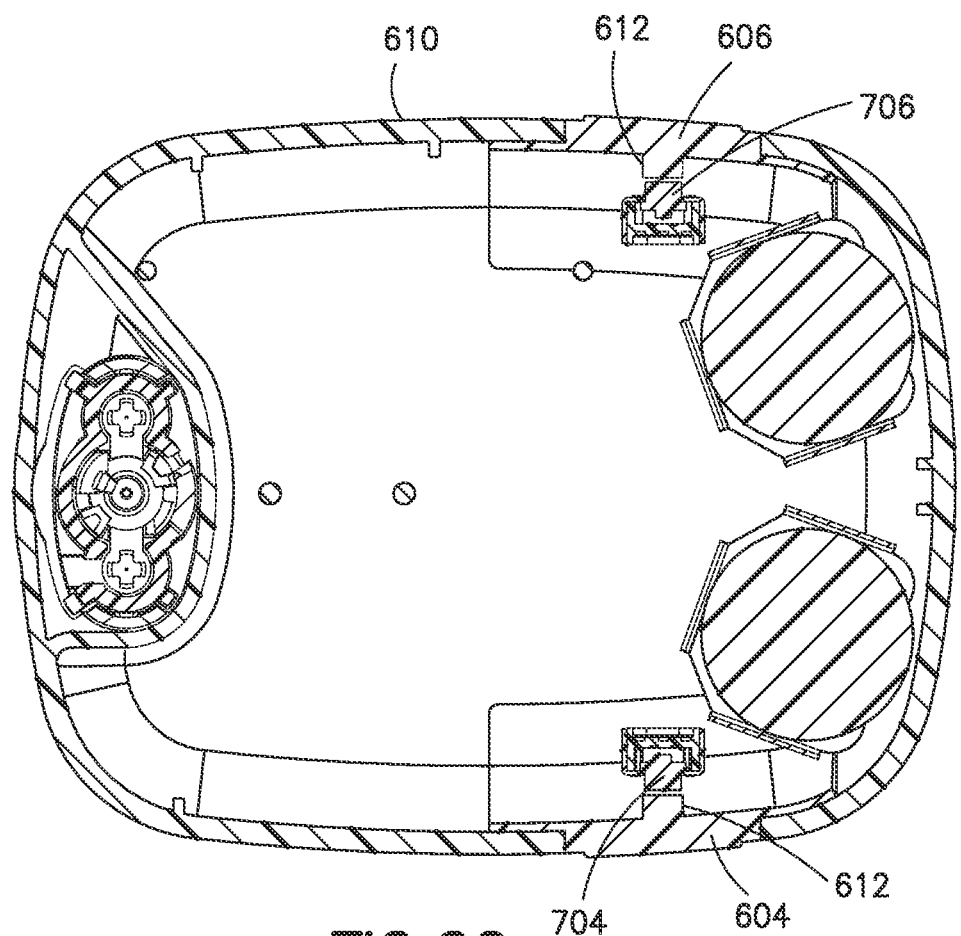
FIG. 22 is a planar section view of the device of FIG. 19 wherein the activation buttons are not activated according to an illustrative implementation of the present invention.

For example, with reference to FIGS. 16-24, an outer housing of a device 600 (e.g., a medicine delivery device such as a patch pump) is provided with elastomer activation buttons 604, 606 according to an illustrative embodiment of the present invention. For example, the outer housing can be formed from a rigid material indicated at 610 such as plastic with holes or cutouts indicated at 608 configured such that the elastomer activation buttons 604, 606 are two shot molded into the space defined by the holes or cutouts 608. The housing 602, switches 704, 706, and elastomer activation buttons 604, 606 are disposed such that, when a user pushes on, depresses or otherwise activates the activation buttons 604, 606, the inner surface of each elastomer activation button 604, 606 pushes the corresponding switch 704, 706 (e.g., a tactile switch or other type of switch 704, 706 mounted on or adjacent to the printed circuit board 708). When depressed, the elastomer activation buttons 604, 606 can push the corresponding switches 704, 706 directly, or indirectly (e.g., via an intervening member not shown), to activate the switch. For example, activation of the switch 704, 706 can be the result of a first part of the switch coming into electrical contact with an electrode or other part of the switch or printed circuit board on or near which the switch is mounted within the device to generate a signal output (e.g., indicating button activation and processed by the controller 1500), thereby changing the switch 704, 706 from an inactive state to an active state). The interior surface of each elastomer activation button 604, 606 can be provided with a rib 612 or other physical attribute as illustrated in FIGS. 17, 18 and 22; however, a rib 612 may not be required depending on the materials used for the buttons 604, 606, the type of switch 704, 706, the arrangement of the housing 602, switch 704 or 706 and button 604 or 606, respectively, relative to each other, and the desired human number factors such as the desired amount of pressure required by the user to activate the switch without false activation and the desired tactile feedback.

Figure 23:
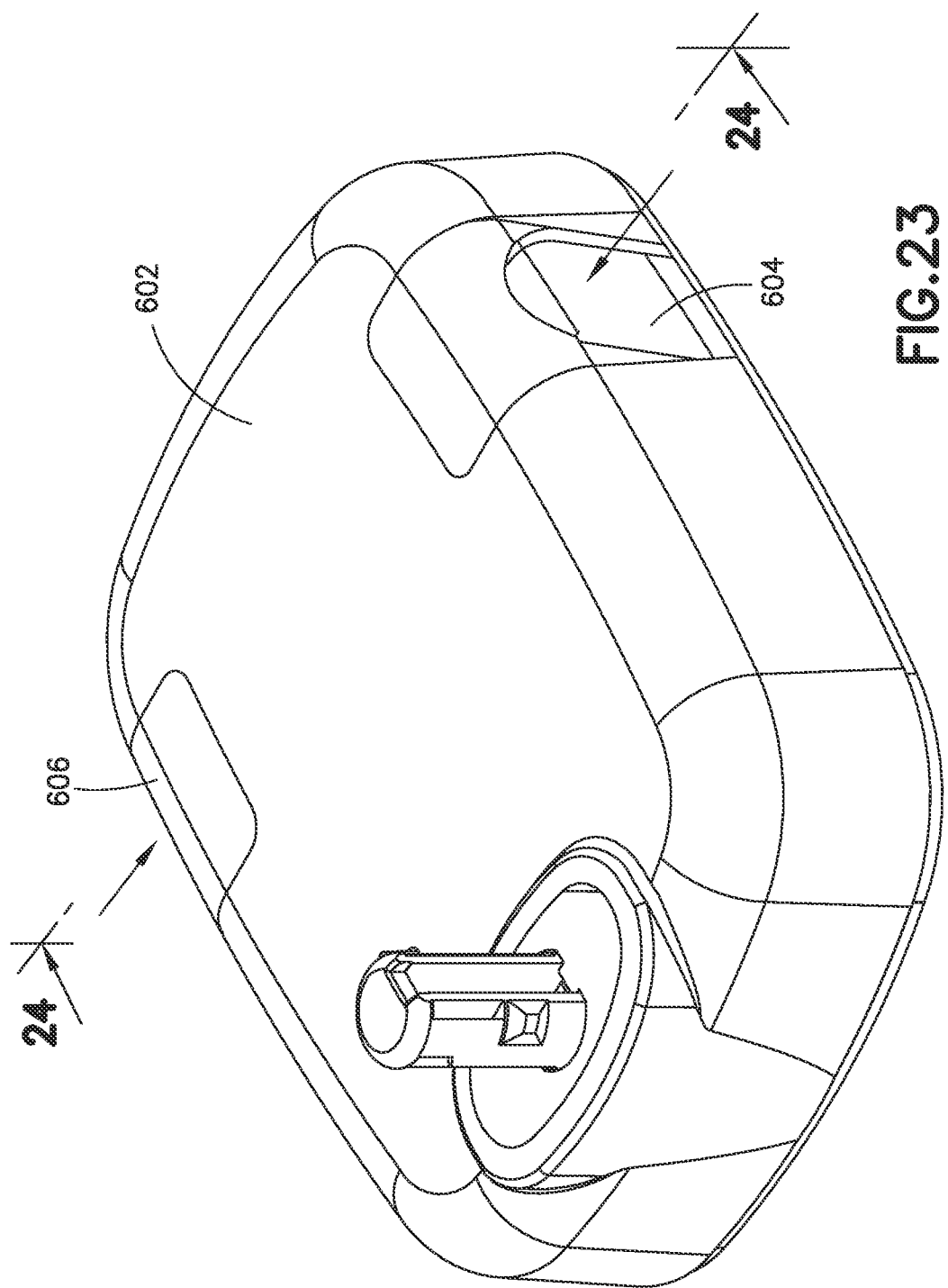
FIG. 23 is a perspective view of the device of FIG. 16 wherein the activation buttons are activated according to an illustrative implementation of the present invention.

As shown in FIG. 17, which is an exploded view of the various components of the device 600, the outer housing 602 has cutouts 608 configured to receive elastomeric buttons 604, 606 which are form fitted to provide sealing against ingress to the interior of the device when assembled. As shown in FIG. 18, which is a bottom view of the outer housing 602, the elastomeric buttons 604, 606 can be formed with a rib 612 to facilitate providing a selected amount or degree of tactile feedback to the user for distinguishing between button activation and non-activation. As illustrated in FIGS. 19, 20, 21 and 22, when the activation buttons are not depressed or otherwise activated, the interior surface of the button 604, 606 (e.g., the rib 612) does not come into contact with the corresponding switch 704, 706 and the switch is, therefore, not activated (e.g., as indicated by the switches 704, 706 being in non-deployed positions as shown in FIG. 22). On the other hand, as shown in FIGS. 23 and 24, when the activation buttons are depressed or otherwise activated, the interior surface of the button 604, 606 (e.g., the rib 612) comes into contact with the corresponding switch 704, 706 and the switch is, therefore, activated (e.g., as indicated by the switches 704, 706 being in deployed positions as shown in FIG. 24 where the tactile part of each switch 704, 706 is translated toward its corresponding electrical contact).

While certain illustrative embodiments of the present invention have been shown and described herein with reference to certain preferred embodiments thereof, it will be understood by those skilled in the art that various changes in form and details may be made therein without departing from the spirit and scope of the invention.

The invention claimed is:

1. A method for infusing a medical substance comprising:
    initiating a first time trace based on a first user input and a second time trace based on a second user input, the first time trace and the second time trace being independent time traces based on said first user input and said second user input, said first time trace comprising a first start time, a first stop time, and a first duration, said second time trace comprising a second start time, a second stop time, and a second duration;
    evaluating said first time trace and said second time trace to command infusing of the medical substance based on a comparison between said first time trace and said second time trace, said comparison depending on at least one of said first start time, said first stop time, said first duration, coinciding with at least one of said second start time, said second stop time, and said second duration; and
    initiating a bolus infusion comprising an amount of the medical substance that is independent of the first duration and the second duration when the comparison between said first time trace and said second time trace indicates a valid bolus activation using said first user input and said second user input.

2. The method of claim 1, further comprising:
receiving said first user input via a first user accessible activation control; and
receiving said second user input via a second user accessible activation control
wherein said initiating comprises
selectively initiating said first time trace based on said first activation control receiving said first user input; and
selectively initiating said second time trace based on said second activation control receiving said second user input.

3. The method of claim 2, wherein
said first user accessible activation control comprises a first user accessible button,
said second user accessible activation control comprises a second user accessible button, and
said first user accessible button and said second user accessible button are configured with respect to a housing.

4. The method of claim 3, wherein said housing comprises a volume containing said medical substance.

5. The method of claim 3, wherein said first user accessible button is disposed at a distance with respect to said second user accessible button, whereby actuation of said first user accessible button is independent of actuation of said second user accessible button.

6. The method of claim 1, wherein any one of said first stop time, said first duration, said second start time, said second stop time, and said second duration comprises at least one of a preset value stored in a non-transient computer readable memory, a value transmitted to a controller via wired and/or wireless communication, and a selectively determined value based on an intended operation of a medical device.

7. The method of claim 1, further comprising initiating a first timer in response to said first user input, and initiating a second timer in response to said second user input, said first time trace and said second time trace corresponding to durations of the first timer and the second timer, respectively.

8. The method of claim 7, wherein the initiating the bolus infusion comprises determining when the duration of the first timer and the duration of the second timer overlap, the comparison between said first time trace and said second time trace corresponding to the overlap.

* * * * *